United States Patent [19]
Brain

[11] Patent Number: 5,249,571
[45] Date of Patent: Oct. 5, 1993

[54] LARYNGEAL CLAMP AIRWAY

[76] Inventor: Archibald I. J. Brain, St. Andrews, Abney Court Drive, Bourne End, Bucks SL8 5DL, United Kingdom

[21] Appl. No.: 875,457

[22] Filed: Apr. 29, 1992

[51] Int. Cl.$^5$ .............................................. A61M 25/00
[52] U.S. Cl. ......................... 128/207.14; 128/200.24; 128/DIG. 26
[58] Field of Search ...................... 128/200.24, 200.26, 128/207.14, 207.15, 207.18, DIG. 26, 898, 15, 17, 3, 4, 5, 6, 10, 11; 604/96

[56] References Cited

U.S. PATENT DOCUMENTS 4,509,514  4/1985  Brain .............................. 128/207.15
5,038,766  8/1991  Parker ............................ 128/200.26

Primary Examiner—Edgar S. Burr
Assistant Examiner—Eric P. Raciti
Attorney, Agent, or Firm—Hopgood, Calimafde, Kalil, Blaustein & Judlowe

[57] ABSTRACT

A clamping mechanism for use in conjunction with or forming an integral part of a laryngeal mask airway, for the purpose of forming a seal between the mask and the entrance to the larynx; the seal is sufficient to overcome the danger of aspiration of regurgitated or vomited matter into the lungs.

28 Claims, 3 Drawing Sheets

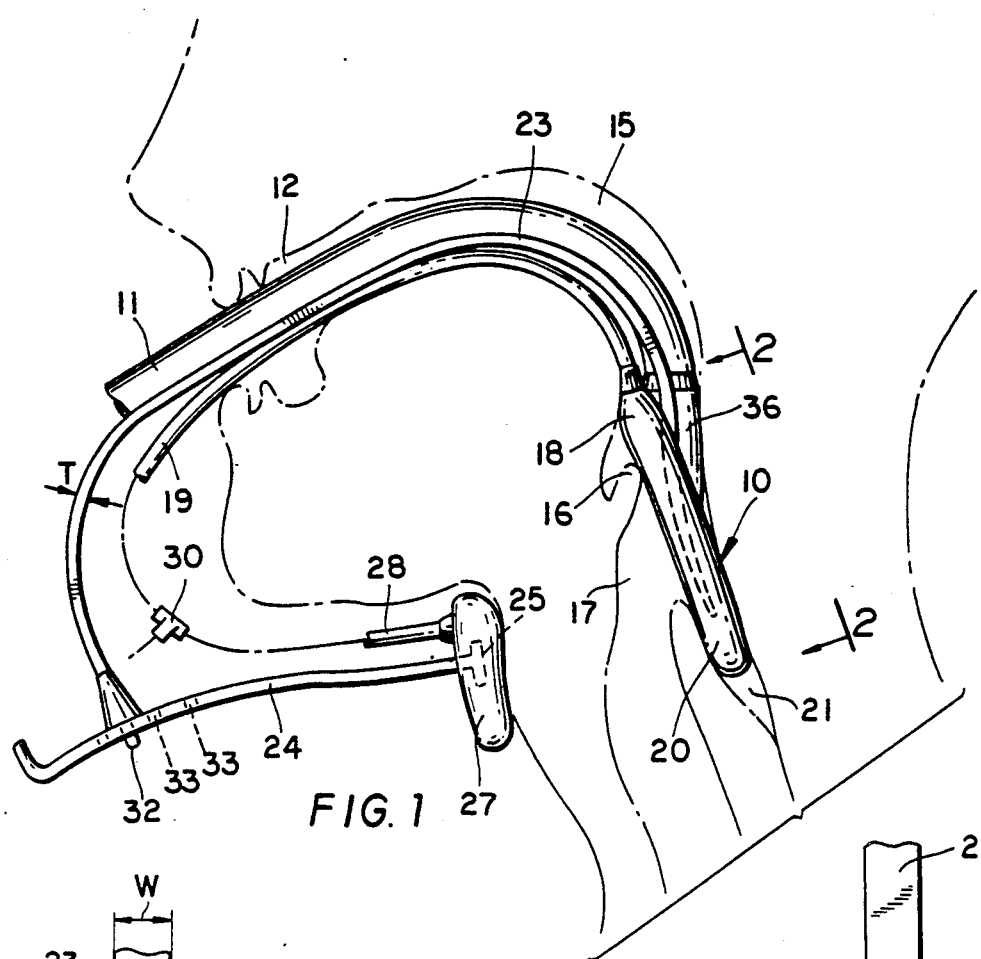
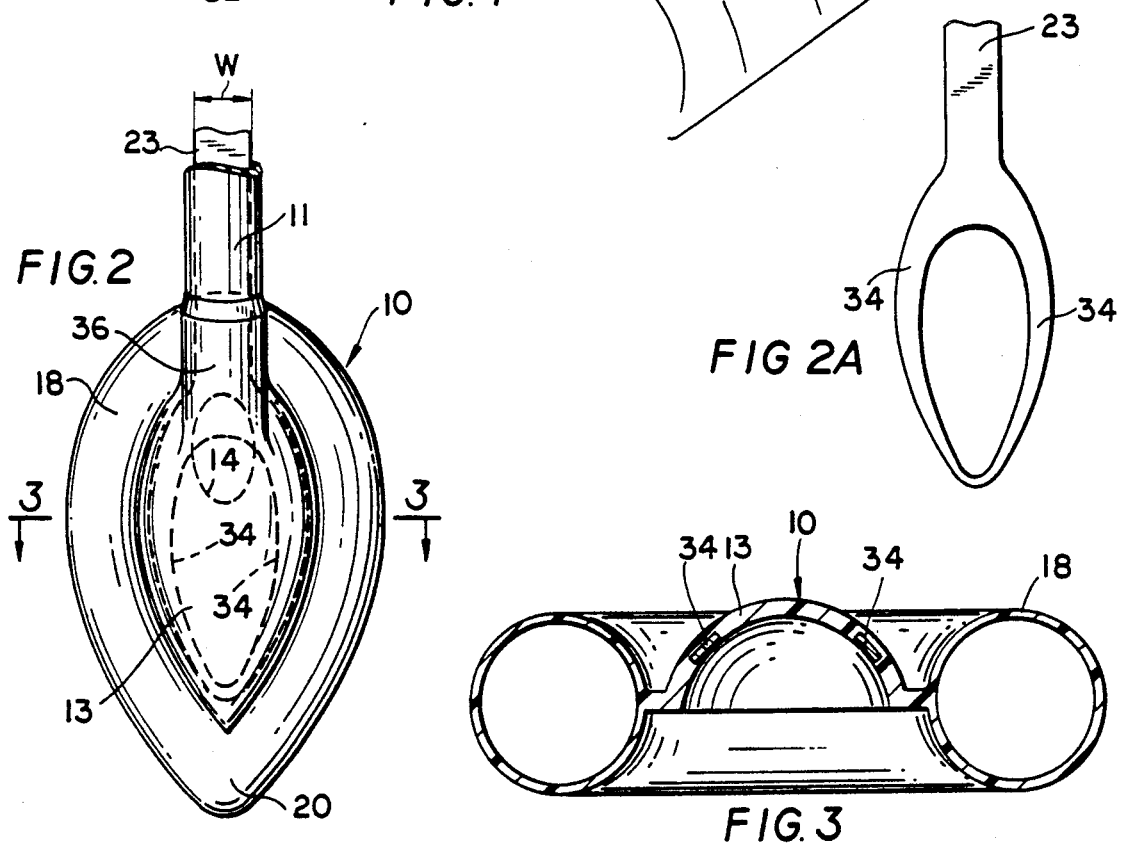

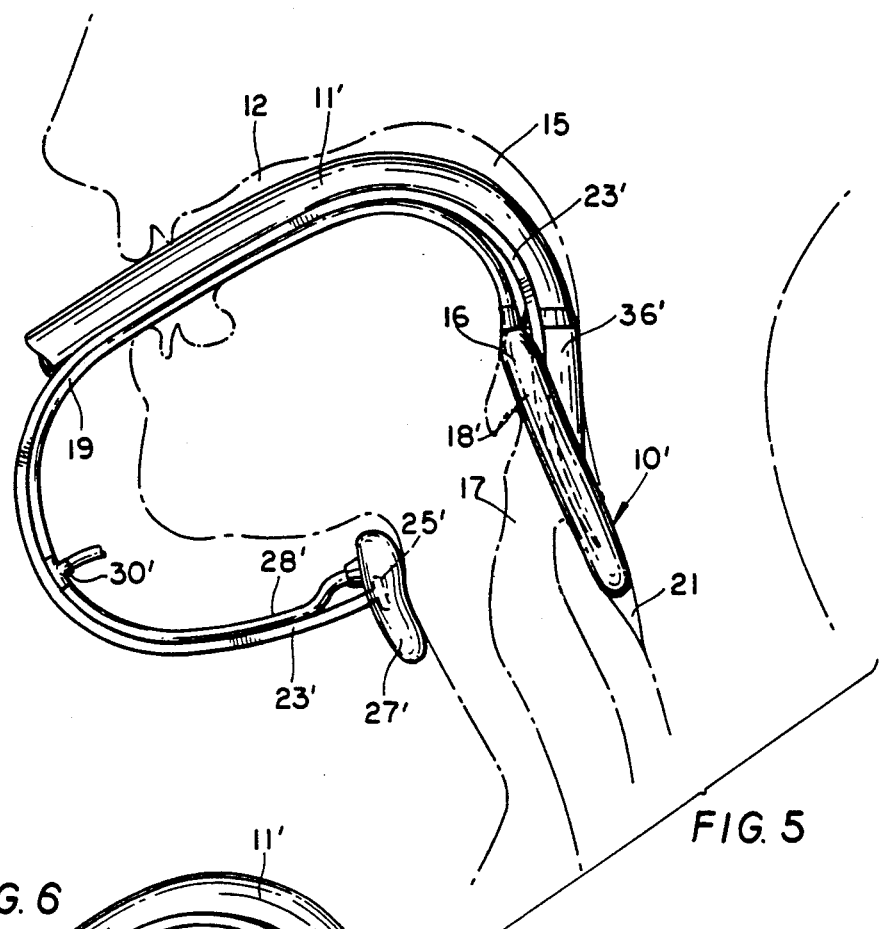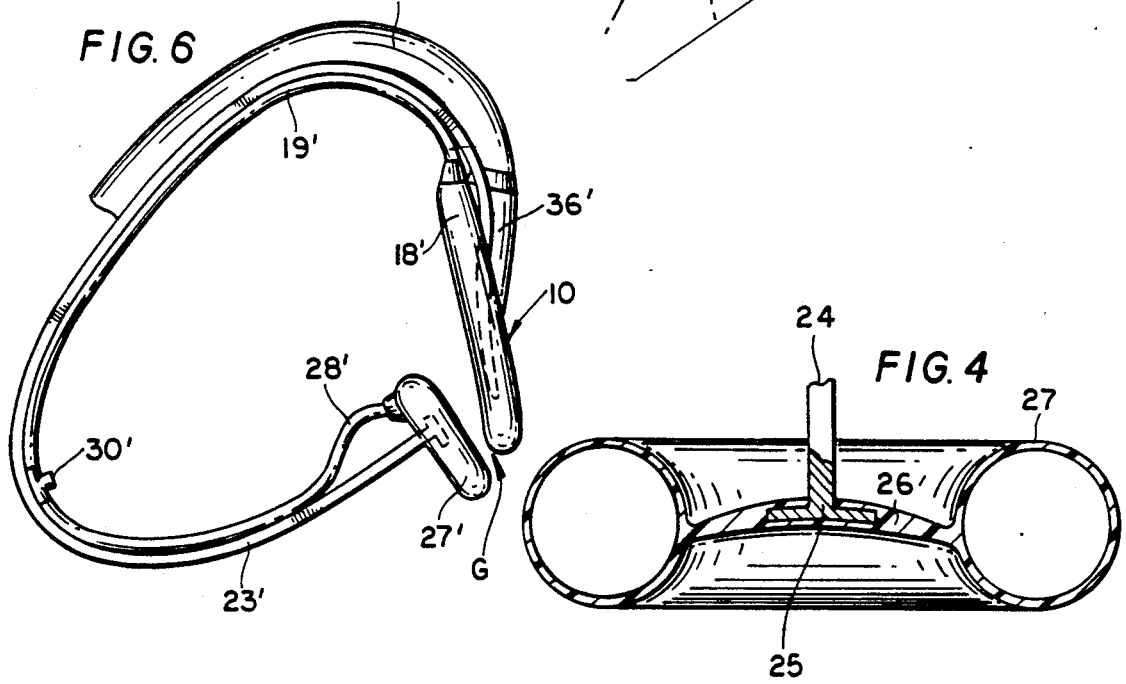

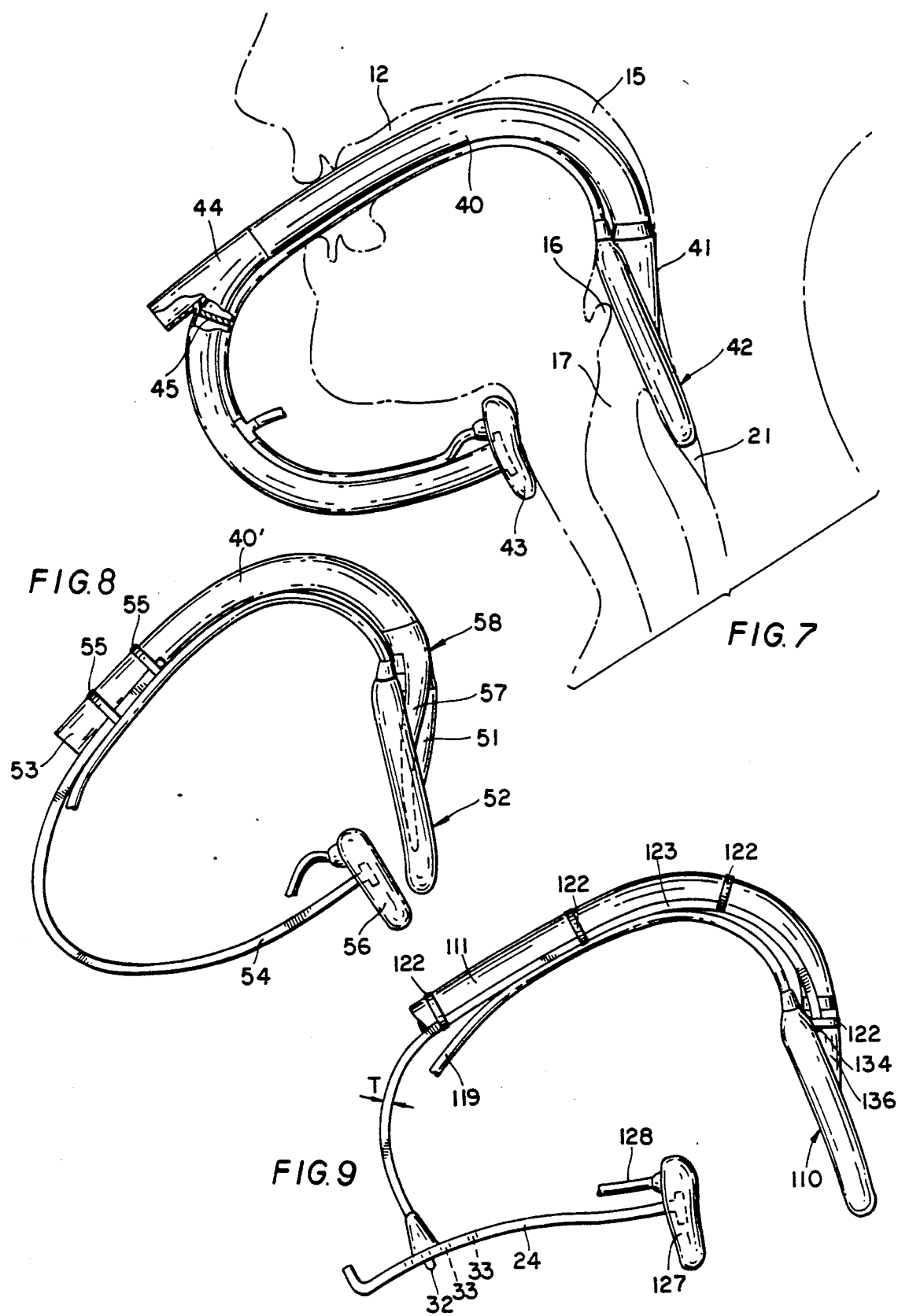

LARYNGEAL CLAMP AIRWAY

BACKGROUND OF THE INVENTION

The invention relates to laryngeal masks, illustratively of the variety disclosed in U.K. Patent 2,111,394B (corresponding to U.S. Pat. No. 4,509,514) and in published U.K. Patent Application No. 2,229,367A (corresponding to U.S. Pat. No. 4,995,388). Such masks are artificial airway devices designed to facilitate lung ventilation in an unconscious patient by forming a low-pressure seal around the laryngeal inlet. The seal surrounds an appropriately shaped mask which fits into the lower pharynx and is attached to a tube which emerges from the mouth, as for connection to medical gas-supply tubing.

In practice, these devices have been successful and are now in daily use in hospitals throughout the United Kingdom. Such masks have been found effective in achieving a reliable airway, preventing obstruction in the unconscious patient. As presently used, such masks are especially effective in cases where difficulty with the airway is experienced. For example, the mask has been found to prevent contamination of the lungs by blood or debris during surgery of the nose or throat. But it has become apparent that an important contraindication to its use is the patient who is at risk from vomiting or regurgitation of stomach contents while unconscious. Although the device forms an inflatable-cuff seal around the laryngeal inlet sufficient to permit inflation of the lungs during artificial ventilation, the seal is not sufficient to prevent lung contamination in the event of retching, vomiting or regurgitation. Patients who are not adequately starved prior to surgery are thus not suitable for use of the laryngeal mask. In such patients, an endotracheal tube is still regarded as affording the safest protection to the patient's airways. However, insertion of an endotracheal tube is not always without difficulty, and failure to make a timely insertion can lead to death or brain damage. In such cases, the laryngeal mask has proven to be life-saving. And, in cases when it has not been possible to safely insert an endotracheal tube, it has been found possible first to install a laryngeal mask, and then to use the tube of the laryngeal mask as a guide, for piloted insertion of an endotracheal tube through the mask.

My U.S. Pat. No. 4,995,388 describes other means associated with a laryngeal mask to prevent aspiration of stomach contents into the lungs. In essence, such means rely upon a combination of improved peripheral continuity of seal pressure against the larynx and the provision of drainage tubing for conduct of gastric contents away from the laryngeal inlet.

Regardless of the specific purpose to be achieved with laryngeal mask in use today, the problem of sealing effectiveness persists. These masks have been designed to fit quite accurately into the lower pharynx, so that when inflated, pressure is exerted on all the surrounding structures to greater or lesser degrees, depending on the resistance they offer to displacement. In broad terms, the structures in front of the mask are cartilaginous; those surrounding the mask are muscular; and those behind the mask are bony. Inflation of the cuff of the mask therefore results in the cartilaginous structures of the larynx being pushed forward, away from the bony structures of neck vertibrae, thus stretching and tensing the surrounding muscles. The seal generated against the laryngeal inlet therefore depends to some extent upon stretch resistance of muscles and soft tissues, as cuff-inflating volume of the mask expands.

If an unconscious patient retches, vomits or regurgitates gastric contents, the balance of forces reacting on the inflated cuff is transiently upset. The muscles surrounding the mask relax, and the sphincteric mechanism at the lower end of the mask also relaxes, with consequent loss or degrading of seal effectiveness; and fluid or semisolids can be forced upward through the oesophagus during such relaxation. Moreover, the larynx is itself displaced upwards as part of the vomiting or retching reflex, and such displacement alone may be sufficient to disrupt the seal of the mask around the laryngeal inlet.

Still further, and of crucial importance, is the fact that the airway tube to which the mask is attached offers resistance to flexure when in its normal position in the patient's pharynx. The airway tube thus exerts a constant force against the bony posterior walls of the pharynx. This means that in the event of a relaxation of the surrounding structures, the mask will tend to remain firmly in contact with the posterior wall. Vomited or regurgitated matter may therefore pass in front of the mask and so enter the laryngeal inlet.

BRIEF STATEMENT OF THE INVENTION

It is an object of the invention to provide a laryngeal-mask system with improved ability to prevent lung soiling by gastric contents.

It is a specific object of the invention to avoid the above-noted transient loss of seal effectiveness by ensuring that seal pressure of the mask against the laryngeal inlet remains unaffected by and is independent of such changes in the surrounding structures as may occur during vomiting, retching or regurgitation.

Stated in other words, it is a specific object of the invention to achieve the above object by enhancing sealing effectiveness of the laryngeal mask around the laryngeal inlet, with little or no reaction upon surrounding anatomical structures.

Another specific object of the invention is to achieve the above objects by relying upon reference to an external part of the patient's body, for enhancement of sealing effectiveness of the laryngeal mask around the laryngeal inlet.

A further specific object is to achieve the foregoing objects with a laryngeal-mask system wherein the enhancement of sealing effectiveness is selectively variable by means external to the patient.

A general object is to achieve the foregoing objects with relatively simple structure which is of minor incremental cost and which is readily and effectively usable, even in the hands of relatively unskilled paramedic personnel.

The invention in a preferred embodiment achieves these objects in a laryngeal mask system of the character indicated wherein a stiffly compliant member, secured to or extending within the tubular air/gas passage of the laryngeal mask, has a seal-loading end configurated to apply mechanical force to air bladder or other cushioning cuff means for establishing a peripheral seal around the laryngeal inlet. The other end of the stiffly compliant member is configured to project externally of the patient, skirting around his chin for application of a cushioned clamp-referencing contact with the neck region which registers with the mask. The external portion of the stiffly compliant structure includes simple mechanism whereby compliant stress in the stiffening member can be selectively adjusted, so that clamping force applied to the laryngeal seal can be selectively adjusted.

DETAILED DESCRIPTION

The invention will be described in detail for a preferred embodiment and for other embodiments, all in conjunction with the accompanying drawings, in which:

FIG. 1 is a diagrammatic view generally in side elevation showing the preferred embodiment of an artificial airway featuring a laryngeal mask of the invention, shown in position for use in a patient;

FIG. 2 is an enlarged fragmentary view of the mask portion of FIG. 1, as seen from the aspect 2—2 of FIG. 1;

FIG. 2A is a view from the aspect 2—2 of FIG. 1, limited to an element of clamp structure of the invention, said element being contained within the mask portion of FIG. 2;

FIG. 3 is a further enlarged sectional view taken at the plane 3—3 of FIG. 2;

FIG. 4 is a sectional view similar to the section of FIG. 3, but for the case of another element of the clamp structure of FIG. 1;

FIG. 5 is a view similar to FIG. 1, for another embodiment of the invention, also in position for use in a patient;

FIG. 6 is a view from the aspect of FIG. 5, but showing the embodiment of FIG. 5 prior to installation in a patient;

FIG. 7 is a view similar to FIGS. 1 and 5, for a third embodiment of the invention;

FIG. 8 is a view similar to FIG. 6, for a fourth embodiment of the invention; and FIG. 9 is a view of apparatus as in FIG. 1, representing modification from FIG. 1.

Referring first to the preferred embodiment of FIGS. 1 to 4, the invention is shown in application to an airway system comprising a laryngeal-mask unit 10 and its flexible airway tube 11 installed through the mouth 12 of a patient. The mask unit 10 may be as described in either of said U.S. patents and therefore need not now be described in detail. It suffices to state that mask unit 10 comprises a body portion 13 having a lumen 14 through which the airway tube 11 can establish a free externally accessible ventilating passage, via the patient's mouth 12 and throat 15, and past the epiglottis 16 to the larynx 17. The body 19 of mask 10 may be of silicone rubber and relatively stiff; and body 13 is surrounded by an inflatable ring or cuff 18 which is circumferentially united to body 13 and which may also be of silicone rubber, although relatively soft and flexible compared to body 13. An externally accessible flexible tube 19 is the means of supplying air to the inflatable ring 18 and of extracting air from (and therefore collapsing) ring 18 for purposes of mask insertion in or removal from the patient. In the installed position shown, the projecting but blunted distal end 20 of ring 18 is shaped to conform with the base of the hypopharynx where it has established locating reference at the upper end of the oesophagus 21, and the inflated ring establishes a peripherally sealed closure around the laryngeal inlet, whereby airway tube 11 communicates only with the larynx 17.

In accordance with the invention, a stiffly compliant member 23, which is suitably of stainless steel, is stressed to provide a clamp function as between (a) its internal or distal end pressing mask 10 (and therefore its inflated ring 18) into preloaded engagement around the laryngeal inlet and (b) its external or proximal end, which has similar but oppositely directed preloaded engagement with a local region of the patient's neck. As shown, the compliant member 23 is one of two adjustably connected parts of the clamp structure, the second part 24 being generally straight and with a base-end formation 25 that is seen in FIG. 4 to be molded into the central body 26 of an inflatable ring or cushion 27. An inflation-air connection 28 to ring 27 is schematically indicated in FIG. 1 for inflation-air supply via a T-fitting 30, in common with air-supply connection 19 to the inflatable ring 18 of mask 10.

More specifically, the stiffly compliant strip of member 23 is shown to be of generally rectangular section, being characterized by a width W (FIG. 2) exceeding its thickness T (FIG. 1), and being suitably a strip of 16-ga. material, of ⅜-inch width. Initially, i.e., before insertion in the patient, the clamp member 23 is prebent a little more than enough to conform approximately to its ultimate course through the mouth, throat and pharynx of the patient; and the portion which extends outside the patient is prebent downwardly to clear the patient's chin and, when connected to part 24, to effectively extend beneath the chin to the point of cushioned clamp reference to the patient's neck. The adjustable connection of parts 23/24 is schematically shown to comprise a projection 32 of member 23, of rectangular section, removably insertable in a selected one of a plurality of spaced rectangular slots 33 along the clamp part 24. A collar formation of member 23, near the projection 32, provides a stop to retain the selected point of adjusted connection, and it will be understood that such selection is made to compliantly stress the bow of member 23 in the widening or opening direction, whereby this compliant stress effects loading force or squeezing action as between body structures engaged at the respective ends or jaws of the clamp. Use of the expression "compliantly stressed" will be understood to mean that such stress results from bending short of the yield point of the involved material, so that after removing the mask, the stress will have been relieved, and the overall structure will return to its originally bent and unstressed condition.

FIGS. 2, 2A and 3 illustrate detail of preferred connection of the internal or distal end of the compliant member 23 to the body 13 of mask 10. As seen separately in FIG. 2A, the distal end of member 13 is bifurcated, to provide spaced and oppositely bowed arms 34 which are tapered for more gentle compliance as they converge to complete a loop at their connected outer ends. FIG. 2 shows this structure in dashed outline because it is embedded in the molding of mask body 13, as seen for the section of FIG. 3. The embedment is such as not to interfere with the ventilation passage afforded through the lumen 14 of mask 10, and compliant flexibility of the looped connection of arms 34 is sufficient to enable negotiation of throat (15) curvature without passing the yield point; thus, once past throat 15, the ends of arms 34 will resume their unstressed state, for safe piloting of mask (10) insertion to the point of entry and location of end 20 at the upper end of the oesophagus 21.

The described structure of the distal-end connection of compliant member 23 to mask 10 will be seen to apply distributed clamping force over the effective longitudinal extent of the relatively stiff body portion 13 of the mask. In particular, in the pharynx region, where body 13 integrally includes the inclined-port formation 36 of connection to airway tube 11, ring-18 inflation would otherwise drive formation 36 for reacting contact with adjacent vertibrae structure, but the provision of at least full-width bearing of strip 23 against relatively soft tissues above the epiglottis ensures that ring-inflation pressure will be emphasized for sealing action against the adjacent region around the laryngeal inlet, while relieving reaction against or upon the bony and muscular structures at the locale of the entrance-port formation. At the same time, the elongate and tapering formation of arms 34 and their reinforcement of the mask body 13 assure distribution of clamping force around the rest of the laryngeal inlet, for enhanced sealing action and for greater if not total independence from the effects of muscular transients associated with retching, vomiting and the like.

The stiffly compliant member 23, in its normal unstressed and bent profile, may be unattached to the airway tube 11 except via the mask (10) connection as described. On the other hand, it is preferred that there be at least several spaced points of connection of member 23 to tube 11 along the length of those parts which are to be installed within the patient. Specifically, present preference is that member 23 be coated with suitable plastic material, such as silicone rubber, and that member 23 be bonded to tube 11, as by coating tube 11 with the same plastic material; such flexing as is involved in installing and removing the mask assembly with respect to the patient, may then involve flexing of tube 11 and member 23 as a single unit.

FIGS. 5 and 6 are directed to another embodiment, which respresents simplification from the adjustable structure of FIGS. 1 to 4. In FIGS. 5 and 6, mask 10' and its connections to airway tube 11' and to the distal end of a stiffly compliant clamp member 23' are as already described. The difference resides in member 23' being the entire clamp, extending outwardly of and around the patient's chin for direct action against the patient's neck; and as best seen in FIG. 6, the preformed bend of member 23' establishes a relatively small gap G between the body-contacting jaw parts 18' and 27' of the clamp, when in unstressed condition. Installation of course requires that gap G be opened, as a compliant spreading of the jaws, while the mask 10 and tube 11 are inserted, with at least ring 18' in deflated and flexibly foldable condition. Once inflated at 18', the laryngeal inlet will have been sealed, and the spring member 23' may be released for compliantly stressed further reference at 27' to the patient's neck, as seen in FIG. 1. If the clamp action is then determined to be less than desired, a simple way to effect enhanced clamp force is to insert a pad of sufficient thickness between inflated ring 27' and the patient's neck, thereby more outwardly expanding member 23' and increasing the level of compliant clamping stress.

The arrangements of FIGS. 7 and 8 are modifications wherein stiffly compliant bending stress for clamp action relies upon such properties as are inherent in the construction of the airway tubes 40 in FIG. 7 and 40' in FIG. 8. In FIG. 7, the single airway tube 40 is connected at its internal or distal end to the inlet-port connection structure 41 of the body of mask 42, as at 36 in FIG. 1; and the proximal or external end of tube 40 is, as with stiffly compliant member 23' in FIG. 6, terminated by an inflatable pad or ring 43. Beyond a location 44 of external ventilation access, the tube 40 has no function other than to provide the preformed general course shown for member 23' in FIG. 6; for this reason, a plug, stop or closure wall 45 is shown in tube 40 adjacent a ventilating Y-formation shown at 44.

A preformed stiffly compliant airway tube 40 is within available skills and is custom-available from various sources in the United Kingdom and/or in the United States. Such tubes of flexible plastic material are rendered into permanently bent unstressed profile, suitable for FIG. 7 purposes by incorporating plural strands of tensed filament into the tube material. The strands of tensed filaments are in circumferentially spaced, distributed array around the tube axis, the strands on the concave portion of the ultimately desired curved shape being strongly tensed relative to those on the opposite or convex portion of the same curve. When the differently tensed filaments have been integrated into the cured tube, as by using a jig or mold to retain the tube in its desired bent shape for the duration of the curing process, the differential tensions of the filaments will thereafter retain the bent shape of the tube as the normal otherwise-unstressed shape. Such a shaped tube provides the compliantly stressed resistance to straightening which is utilized for clamp action in FIG. 7.

In the arrangement of FIG. 8, the preformed and bent airway tube 40' is only of the limited longitudinal extent needed to accommodate the ventilation purposes already described for the laryngeal mask 52, to the point of external venting, here shown extending tangentially, at 53. The remainder of stiffly compliant clamp action is provided by a stiffly compliant strip 54, as of stainless steel, spliced by spaced circumferential ties or bands 55 to tube 40', and extending to the inflatable ring 56 for neck-referencing contact. Distal-end connection to mask 52 may be as indicated at 41/42 in FIG. 7, but FIG. 8 serves additionally to illustrate that the airway tube (40') connection to mask 52 may be reinforced and locally stiffened by incorporating outwardly bowed metal arms 57 into the molded-body portion of mask 52, said arms being interconnected at their distal end, in the manner described in connection with mask 10. To this end, a metal fitting 58 is locally banded to tube 40' near the inlet-port formation 51, and two bowed arms 57 of this fitting 58 are embedded in the mask body for longitudinally distributed application of clamping force around the laryngeal inlet. Clamp action and its selective adjustment are as for the other described embodiments of the invention.

The tube, mask and clamp components of the various embodiments of the invention will be recognized as being made of sterilizable materials, and it will also be recognized that other sterilizable materials can be used. Such other materials can be selected for greater rigidity than is provided by the silicone rubber mentioned above. Drainage tubes have not been described but may be fixed to the mask as in certain of my other disclosures, but it will be understood that since the present clamp action substantially relieves mask contact of the inflatable ring with structures other than the laryngeal inlet, it is a simpler task to introduce drainage tubes to and past the mask, i.e., after the laryngeal mask has been placed in position.

Although present preference has been indicated for concurrent inflation of the two bladder rings 18, 27, it will be understood that others may prefer to make separate inflation and/or deflation of these components. In such case, it will be understood that a separate stopcock or clamp should be provided in each of the air-supply/exhaust lines 19, 28, and that the T-connection 30 will not be needed.

Although in FIG. 8, the present stiff clamp member 54 has been described as being connected to airway tube 40' by circumferential ties 55, this portion of FIG. 8 can also be taken to illustrate an assembly wherein the involved end of member 54 is merely frictionally guided by bands 55, so that the effective unstressed gap between the inflatable locales of clamp-jaw (52, 56) contact with the patient's body can be selectively adjusted by the extent to which the involved end of member 54 has telescoped insertion through bands 55.

It will be understood that the term "stiffness" as applied to the unstressed bend of described clamp structures is a relative term, in that sufficient clamp loading of the seal around the laryngeal inlet may in certain cases result merely, or to the greatest extent, by having inflated the rings (18, 27) after the mask (10) has been correctly positioned; in that case, the bending displacement involved in compliant stress in member 23 will be relatively small.

FIG. 9 will be seen to illustrate a feature of the invention wherein clamp structure involving members 123, 124, 125 are components of an accessory kit, lending itself to ready assembly to the airway tube 111 and mask 110 of an existing laryngeal-mask assembly, as of the nature described in either of the above-mentioned U.S. patents. Thus, to adapt an existing system 110, 111 to the clamp feature of the invention, a plurality of spaced circumferential-tie bands 122, may be used, as of thin, sterilized, adhesive tape; a set of such bands or a roll of such tape may be a component of the clamp-accessory kit. As shown, there are four such bands 122, the distal one of which anchors shortened bifurcated ends 134 of member 123 to the inlet-port structure of the body of mask 110. Also as shown, a separate air-inflation supply line 128 is provided for the additional inflatable component, it being understood that the existing mask assembly 110, 111 already includes its own inflation-supply line 119.

It will also be understood that the use of stiffening arms 34 or 57 embedded in the mask body is merely illustrative, in that the need for such a measure may be obviated by selection of a maximally hard silicone as the material of the mask body 13, which is sometimes referred to as the back plate of the mask.

What is claimed is:

1. An artificial airway device to facilitate a patient's lung ventilation comprising an airway tube connected at one end thereof to a laryngeal mask, said mask having seal means about the circumference thereof for sealingly engaging the laryngeal inlet of a patient, said seal means being a flexible annular formation surrounding a hollow interior space or lumen of the mask into which the airway opens, and clamp means for biasing said seal means into sealing engagement with the laryngeal opening, said clamp means having a relatively stiff compliant member with an inner end and an outer end, said inner end being connected to said laryngeal mask and defining an inner jaw of the clamp means, said outer end defining an outer jaw, wherein said laryngeal mask is in sealing engagement with the patient's laryngeal inlet, the compliant member extends externally from the patient's mouth and the outer jaw engages the anterior surface of the patient's neck.

2. The airway device of claim 1, in which said annular formation is inflatable and in which the outer end of said clamp means terminates in cushioning means comprising an inflatable pad, and a common means of inflation-air supply connected both to said annular peripheral formation and to said outer-end pad.

3. The airway device of claim 1, in which said compliant means is a single strip of relatively stiffly compliant material, extending from its inner-end mask connection to its outer-end location of neck engagement, said compliant member in uninstalled and unstressed condition being characterized by closer adjacency of said ends than when in stressed installed condition.

4. The airway device of claim 1, in which said clamp means comprises two component elements having selectively adjusting interconnection at a location intermediate said inner and outer ends.

5. The airway device of claim 1, in which said clamp means comprises two component elements having selectively adjusting interconnection at a location external to the patient.

6. The airway device of claim 1, in which said compliant means is secured to said airway tube at least for the course thereof that is adapted for installation in the patient.

7. The airway device of claim 1, in which the outer end of said clamp means carries cushioning means for neck engagement.

8. The airway device of claim 7, in which said cushioning means comprises an inflatable pad.

9. The airway device of claim 7, in which said cushioning means is a circumferentially continuous annular member of resiliently yieldable material connected to and surround a central plate which terminates the outer end of said clamp means.

10. The airway device of claim 9, in which said annular member is inflatable.

11. The airway device of claim 1, in which said mask comprises a molded relatively stiff convexly crowned body continuously connected to and within said flexible annular formation and providing a concave inner volume that is adapted to face the patient's laryngeal inlet, the airway tube communicating directly with a portion of the inner volume of said crowned body; and in which at least the portion of said compliant member that is adapted for installation within the patient is a single piece of strip material that is bifurcated to define spaced outwardly bowed arms that are connected at their distal ends, said arms straddling the airway tube at connection to the body of said mask, and said arms being reinforcing elements in molded consolidation with said mask body.

12. The airway device of claim 11, in which said arms are tapered for reduced stiffness in the distal direction.

13. The airway device of claim 11, in which said mask body is of molded silicone rubber.

14. The airway device of claim 13, in which said flexible annular peripheral formation is an inflatable annulus of silicone rubber that is softly resilient as compared with the silicone rubber of said mask body.

15. The method of installing in a patient a laryngeal mask having a body at one end of an airway and an inflatable flexible annulus surrounding said body and sized for sealing engagement around the patient's laryngeal inlet, which method comprises the steps of:
   (a) deflating the flexible annulus;
   (b) inserting the mask via the throat to the point at which the mask body faces the laryngeal inlet;
   (c) inflating the flexible annulus of the mask to the point of pressurized resilient sealing engagement of the flexible annulus around the laryngeal inlet, in reaction to correspondingly pressurized resilient engagement of the flexible annulus to opposed wall structure of the trachea and of the oesophagus; and (d) applying a clamping force to the mask body in the direction of increasing the resilient load of flexible-mask engagement around the laryngeal inlet while also decreasing resilient reaction loading against wall structure of the trachea and of the oesophagus.

16. The method of claim 15, wherein step (d) comprises the steps of:

(i) selecting an elongate stiffly compliant member of length sufficient to bear against the mask body and to extend through the patient's throat and mouth with airway conformance and externally of the patient, the compliant member in unstressed condition being bent to a greater extent than necessary for airway conformance and for external extension around the chin to a point of neck-referencing contact in generally opposed registration with the laryngeal mask, and (ii) compliantly stressing said member in an incrementally unbending direction to the point of establishing the neck-referencing contact.

17. The method of claim 16, including the further step of providing a resilient pad at the location of neck-referencing contact.

18. The method of claim 17, wherein the resilient pad is inflatable and is inflated to substantially the inflation pressure of the flexible annulus of the mask.

19. The method of claim 15, wherein step (d) comprises the steps of:

(i) selecting an elongate stiffly compliant member of length sufficient to bear against the mask body and to extend through the patient's throat and mouth and externally of the patient, the compliant member in unstressed condition being bent to a greater extent than necessary for airway conformance and for downward external extension at least to the lower part of the chin;

(ii) selecting a neck-referencing member for adjustable connection at one end to the external end of said stiffly compliant member;

(iii) applying the other end of said neck-referencing member to the neck in generally opposed registration with the laryngeal mask; and (iv) compliantly stressing said stiffly compliant member in the unbending direction by adjusted extension of the point of connection of said members.

20. The method of claim 19, including the further step of providing a resilient pad at the location of neck-referencing contact.

21. The method of claim 20, wherein the resilient pad is inflatable and is inflated to substantially the inflation pressure of the flexible annulus of the mask.

22. An artificial airway device to facilitate a patient's lung ventilation, comprising an airway tube connected at one end thereof to a laryngeal mask, said mask having seal means about the circumference thereof for sealingly engaging the laryngeal inlet of a patient, and clamp means for biasing said seal means into sealing engagement with the laryngeal inlet, said clamp means having a relatively stiff compliant member with an inner end and an outer end, said inner end being connected to said laryngeal mask and defining an inner jaw of the clamp means, said outer end being padded and defining a padded outer jaw, wherein when said laryngeal mask is in sealing engagement with the patient's laryngeal inlet, the compliant member extends externally from the patient's mouth and the padded outer jaw engages the anterior surface of the patient's neck.

23. An artificial airway device to facilitate a patient's lung ventilation, comprising an airway tube connected at one end thereof to a laryngeal mask, said mask having seal means about the circumference thereof for sealingly engaging the laryngeal inlet of a patient, and clamp means for biasing said seal means into sealing engagement with the laryngeal inlet, said clamp means having a relatively stiff compliant member and a second member, said compliant member having an inner end and an outer end, said inner end being connected to said laryngeal mask and defining an inner jaw of said clamp means, said outer end being connected to said second member at one end thereof by selectively adjusting means for adjusting the relative orientation of the compliant member and the second member, said second member being padded at the other end thereof and defining a padded outer jaw, wherein when said laryngeal mask is in sealing engagement with the patient's laryngeal inlet, the compliant member extends externally from the patient's mouth and the padded outer jaw engages the anterior surface of the patient's neck.

24. An artificial airway device to facilitate a patient's lung ventilation, comprising an airway tube connected at one end thereof to a laryngeal mask, said mask having seal means about the circumference thereof for sealingly engaging the laryngeal inlet of a patient, said airway tube being relatively stiffly compliant and in unstressed condition being bent at least to the extent providing substantial conformance to the patient's airway and projecting externally at its outer end for ventilation external to the patient's mouth, and clamp means including a connection to the externally projecting end, said clamp means being adapted for padded neck-referencing contact in generally opposed registration with the laryngeal mask and for compliantly stressing the airway tube in the unbending direction.

25. An artificial airway device to facilitate a patient's lung ventilation, comprising an airway tube connected at one end thereof to a laryngeal mask, said mask having seal means about the circumference thereof for sealingly engaging the laryngeal inlet of a patient, said airway tube being relatively stiffly compliant and in unstressed condition being bent at least to the extent providing substantial conformance to the patient's airway and projecting externally at its outer end for ventilation external to the patient's mouth, and clamp means including a connection to the externally projecting end, said clamp means being adapted for neck-referencing contact in generally opposed registration with the laryngeal mask and for compliantly stressing the airway tube in the unbending direction.

26. The artificial airway device of claim 22 or claim 23 or claim 24, in which the seal of said mask extends with peripheral continuity around said mask and is inflatable, in which said padded end is inflatable, and in which a common means of inflation-air supply is connected both to said inflatable seal and to said inflatable pad.

27. An artificial airway device to facilitate a patient's lung ventilation, comprising an airway tube connected at one end thereof to a laryngeal mask, said mask having seal means about the circumference thereof for sealingly engaging the laryngeal inlet of a patient, and clamp means for biasing said seal means into sealing engagement with the laryngeal inlet, said clamp means having a relatively stiff compliant member with an inner end and an outer end, said inner end being connected to said laryngeal mask and defining an inner jaw of the clamp means, said outer end defining an outer jaw, wherein when said laryngeal mask is in sealing engagement with the patient's laryngeal inlet, the compliant member extends externally from the patient's mouth and the outer jaw engages the anterior surface of the patient's neck.

28. An artificial airway device to facilitate a patient's lung ventilation, comprising an airway tube connected at one end thereof to a laryngeal mask, said mask having seal means about the circumference thereof for sealingly engaging the laryngeal inlet of a patient, and clamp means for biasing said seal means into sealing engagement with the laryngeal inlet, said clamp means having a relatively stiff compliant member and a second member, said compliant member having an inner end and an outer end, said inner end being connected to said laryngeal mask and defining an inner jaw of said clamp means, said outer end being connected to said second member at one end thereof by selectively adjusting means for adjusting the relative orientation of the compliant member and the second member, said second member being padded at the other end thereof defining an outer jaw, wherein when said laryngeal mask is in sealing engagement with the patient's laryngeal inlet, the compliant member extends externally from the patient's mouth and the outer jaw engages the anterior surface of the patient's neck.

* * * * *